US012799442B2

(12) United States Patent
Vogel et al.

(10) Patent No.: US 12,799,442 B2
(45) Date of Patent: Nov. 17, 2026

(54) BIOREACTOR FOR THE CULTIVATION OF CELLS

(71) Applicant: FRAUNHOFER-GESELLSCHAFT ZUR FÖRDERUNG DER ANGEWANDTEN FORSCHUNG E.V., Munich (DE)

(72) Inventors: Simon Vogel, Aachen (DE); Stefan Schillberg, Aachen (DE)

(73) Assignee: FRAUNHOFER-GESELLSCHAFT ZUR FÖRDERUNG DER ANGEWANDTEN FORSCHUNG E.V., Munich (DE)

( * ) Notice: Subject to any disclaimer, the term of this patent is extended or adjusted under 35 U.S.C. 154(b) by 948 days.

(21) Appl. No.: 17/794,383

(22) PCT Filed: Jan. 23, 2021

(86) PCT No.: PCT/EP2021/051538
§ 371 (c)(1),
(2) Date: Jul. 21, 2022

(87) PCT Pub. No.: WO2021/148663
PCT Pub. Date: Jul. 29, 2021

(65) Prior Publication Data

US 2023/0050194 A1 Feb. 16, 2023

(30) Foreign Application Priority Data

Jan. 23, 2020 (EP) .................................... 20153266

(51) Int. Cl.
*C12M 1/00* (2006.01)
*C12M 1/12* (2006.01)
*C12M 1/42* (2006.01)

(52) U.S. Cl.
CPC ............ *C12M 23/26* (2013.01); *C12M 25/02* (2013.01); *C12M 29/06* (2013.01); *C12M 35/04* (2013.01)

(58) Field of Classification Search
None
See application file for complete search history.

(56) References Cited

U.S. PATENT DOCUMENTS

2007/0269789 A1 11/2007 Covelli et al.
2013/0089890 A1* 4/2013 Pflanz .................... B01L 3/508 435/287.7

(Continued)

FOREIGN PATENT DOCUMENTS

CA 2801768 A1 7/2014
WO WO-2018087558 A1 * 5/2018 ........... C12M 41/44

OTHER PUBLICATIONS

PCT/EP2021/051538 International Search Report mailed Mar. 23, 2021.

*Primary Examiner* — Michael A Marcheschi
*Assistant Examiner* — Ashley Lopezlira
(74) *Attorney, Agent, or Firm* — Biotech Beach Law PC; Raymond Wagenknecht

(57) ABSTRACT

A bioreactor for the cultivation of cells, comprising at least one vessel which is designed to accommodate cells to be cultivated and at least one culture medium in a vessel interior enclosed at least partially by walls of the vessel in relation to an environment, and comprising a movement device which can be connected to a drive unit and at least partially moves the cells to be cultivated or applies a force to same. An elastic element is arranged in the vessel interior, which is configured such that at least one part of the culture medium can be received at least in a region of the elastic element, and the cells to be cultivated at least intermittently adhere in and/or on at least sections of the elastic element, (Continued)

and the movement device is designed to at least intermittently deform the elastic element.

14 Claims, 4 Drawing Sheets

(56) References Cited

U.S. PATENT DOCUMENTS

| | | | | |
|---|---|---|---|---|
| 2013/0270165 | A1* | 10/2013 | Shevitz | B01D 61/58 210/205 |
| 2015/0252317 | A1 | 9/2015 | Lipkens et al. | |
| 2015/0376560 | A1* | 12/2015 | Finlay | C12N 5/0697 435/378 |
| 2018/0155667 | A1* | 6/2018 | Stobbe | C12M 47/10 |
| 2019/0048305 | A1* | 2/2019 | De | C12M 29/10 |

* cited by examiner

BIOREACTOR FOR THE CULTIVATION OF CELLS

CROSS REFERENCE TO RELATED APPLICATIONS

This is a US national phase application under 35 U.S.C. § 371 of international PCT application No. PCT/EP2021/051538, filed Jan. 23, 2021, which claims priority to European patent application no. 20153266.0, filed Jan. 23, 2020; the content of each is herein incorporated by reference in their entirety.

TECHNICAL FIELD

The invention relates to a bioreactor for the cultivation of cells. The bioreactor described has at least one vessel in which the cells to be cultivated and at least one culture medium are arranged, and a movement device which can be connected to a drive unit and which at least intermittently moves the cells to be cultivated or applies a force to them.

BACKGROUND OF THE INVENTION

A cell culture is the cultivation of animal or plant cells in a culture medium outside the organism. Such cell cultures can propagate cells of a tissue type indefinitely, wherein immortalized, thus, immortal cell lines as well as primary cells are cultivated. When cultivating cells of prokaryotic or eukaryotic origin, the creation of the physiological parameters adapted to the respective cell type, which parameters must at least largely correspond to the respective normal life processes, is of crucial importance. The determination of suitable physiological parameters is important in order to achieve optimal growth behavior, thus, for example, the formation of a cell group or the desired cell shape, a high growth rate, or the production of selected ingredients. For example, in the production of antibiotics, biofilms, thus, cell groups adhering to the surface of culture vessels are often used to modulate the metabolic pathway of the cells and to stimulate antibiotic production.

Furthermore, in the cultivation of cells, in particular mammalian cells, it is well known that electrical or mechanical stimuli or even cell type-specific structures are required for specialized cell types to induce a desired growth. For example, electrical or physical stimuli are required to form myocardioblasts or muscle cells, which then form spindle-shaped cells that assemble into muscle fibers.

To cultivate cells of prokaryotic or eukaryotic origin, various culture vessels, also known as bioreactors, in which the cells are cultivated under aerobic or anaerobic conditions, have been used to date. Known bioreactor systems are shaken cultures or fermenters, in which the cells are supplied with oxygen and nutrients under gassing and stirring or shaking in a nutrient solution. Cultivating the cells is usually done in suspension. By adding carrier materials, large surfaces can be used to form a film.

Another commonly used form of cell cultivation uses fixed-bed reactors, in which a cell suspension flows through a solid bulk or packing. This process is mainly used industrially, for example to propagate cells on a surface matrix and to stimulate them to excrete metabolic products.

A bioreactor used to cultivate microorganisms, cells or cell-free expression systems is known from WO 03/012027 A1. In the described bioreactor, biological or biochemical reactions are carried out, which are used in the field of biotechnology, food technology and environmental protection. The bioreactor described in this publication has a plurality of openings which are used, in particular, for supplying gases or liquids, for taking samples and for supplying microorganisms or cells, the corresponding openings being closable with the aid of suitable closing means. Furthermore, the described bioreactor has a foldable or inflatable insert, which is intended to enable efficient and turbulent mixing of the reaction liquids. Here, special baffles are provided to ensure effective gassing during a circular movement of the insert and the movement of the reaction liquids caused thereby.

SUMMARY OF THE INVENTION

Based on the bioreactors known from the prior art, it is an object of the invention to refine such a culture vessel in such a manner that a high yield can be achieved in cell cultivation due to a suitable initiation of stimuli. In particular, it should be possible to grow special cell groups, such as muscle fibers, which require the application of external stimuli, on a comparatively large scale and also to enable the production of three-dimensional tissue structures in this manner. A corresponding bioreactor should further be suitable to use muscle fibers as starting material for the production of artificial cultivated meat. Furthermore, the device to be specified, thus, the bioreactor, should be able to meet the need for apparatuses that are constructed in a comparatively simple manner and can be scaled or parallelized with respect to the achievable cell yield, in which cells can be grown and the required physical parameters can be applied as needed. First and foremost, the bioreactor to be specified should be implementable for this purpose using relatively simple construction means and using known components so that the cultivation of comparatively large cell groups is also possible taking into account economic boundary conditions.

A bioreactor for the cultivation of cells designed according to the invention has at least one vessel which is suitable for accommodating the cells to be cultivated and at least one culture medium and has a movement device which can be connected to a drive unit and by means of which the cells to be cultivated can be moved at least intermittently or can be subjected to a force. According to the invention, the bioreactor is characterized in that an elastic element is arranged in a vessel interior which is at least partially enclosed by walls of the vessel against an environment, which elastic element is configured in such a manner that it can receive culture medium at least partially and at least for a certain period of time, and the cells to be cultivated adhere at least intermittently in and or to the elastic element, and in that the movement device is adapted to at least intermittently deform the elastic element, in particular to compress it at least in certain regions.

Thus, essential for the invention is an elastic element that can at least intermittently receive culture medium and be deformed, in particular compressed, by means of at least one specifically drivable movement device. Preferably, the deformation of the elastic element to which the cells to be cultivated adhere takes place in such a manner that during a compression of the element, the culture medium is expelled from the element while the element takes up, in particular absorbs, culture medium in an at least partially relaxed state. By such alternating suction and expulsion of culture medium, the cells adhering to or in the elastic element can be reliably and uniformly supplied with the nutrients contained in the culture medium, without a supply of gas, for example oxygen, being impeded thereby.

Cells to be cultivated are arranged on or in the elastic element, at least in certain region, which cells are stimulated in a suitable manner by movement stimuli due to the deformation of the elastic element, thereby promoting the cultivation of these cells. The deformation, in particular compression, of the elastic element can take place continuously at successive intervals or within varying time intervals. Likewise, it is conceivable to apply a uniform force or a variable force to the elastic element so that the deformation of the elastic element varies in type and/or strength between at least two successive deformation processes. In general, a device designed according to the invention is suitable for cultivating both prokaryotic and eukaryotic cells. Likewise, it is conceivable that such a device could be used for the production of antibiotics and/or used in the field of pharmacological evaluation of active substances. Furthermore, a device using the invention is preferably suitable for implementing a biofilm fermentation. Thus, a variety of different applications as well as the implementation of different biochemical or molecular biological processes based on the use of the abstract inventive idea are feasible.

In a special embodiment of the invention, it is provided that the elastic element comprises at least partially sponge-like material. Depending on the cells to be cultivated, it can be advantageous here if the sponge-like material is a synthetically produced sponge, to the surface and/or in the pores of which the cells to be cultivated adhere, at least in certain regions. Preferably, the sponge-like material comprises at least one foam, wherein it is generally conceivable that the surface of the sponge-like material, in particular of the foam, is surface-treated, for example coated, at least in certain regions.

Alternatively or additionally, it is conceivable that the elastic material at least partially comprises in vitro meat, bacteria, prokaryotic cells, at least one polymer, a protein structure, such as a silk protein structure, glucomannan, zein, collagen, alginate, chitosan and/or cellulose. It is always essential to the invention that the elastic element is deformed, in particular compressed, by means of a specifically movable movement device, so that the cells to be cultivated are stimulated in a suitable manner by movement stimuli and are thus stimulated to grow and/or an effective supply of nutrients to the cells to be cultivated is ensured.

According to a particular embodiment of the invention, the movement device closes off the vessel interior of the bioreactor from the environment, at least in certain regions. In this context, it is conceivable that the movement device has at least one piston which is arranged to be movable in certain regions along an inner wall of the vessel. Preferably, in this case, at least one sealing element, for example in the form of an annular seal, is provided between the movable piston and the inner wall of the vessel. It is conceivable in this context that a component of the movement device connected to the elastic element has a sealing surface which, together with the housing wall, encloses a sealing element, or that a special drive element of the movement device which has a comparatively small sealing surface, such as a piston rod connected to a piston, encloses a sealing element between itself and the vessel wall.

Again, it is essential to the invention that the movement device, for example the piston, is coupled to the elastic element in such a manner that, due to the movement of the movement device, the elastic element is deformed, wherein the elastic element is alternately compressed and then relaxed. Due to these movements, the cells to be cultivated, which are arranged at least in certain region on or in the elastic element, are stimulated with a movement stimulus that promotes the growth of the cells. Likewise, the compression causes culture medium contained in the elastic element to be expelled from it and then culture medium from the vessel interior is absorbed by the relaxed elastic element.

Furthermore, it is advantageous if the vessel interior has an inlet and/or an outlet, so that at least one fluid-tight flow channel is created between the vessel interior and a fluid outlet and/or inlet or the environment. Via such inlets and/or outlets, gases and/or liquids required for establishing the physiological parameters in the vessel interior necessary for cultivating the cells can preferably be selectively introduced into the vessel interior and discharged again. Preferably, a valve is provided in the inlet and/or in the outlet, which can be opened and closed in response to a control signal. It is of particular advantage if a valve arranged in the inlet and/or in the outlet is opened and closed as a function of a pressure prevailing in the vessel interior, which can be a positive or a negative pressure with respect to an environment and/or a fluid supply system.

According to a very particularly suitable refinement of the invention, a bioreactor designed according to the invention has both an inlet with an inlet valve and an outlet with an outlet valve, wherein both the valve in the inlet and the valve in the outlet are opened and closed as a function of a pressure prevailing in the vessel interior, which can be an overpressure or a negative pressure compared to a fluid supply system connectable to an environment and/or to the vessel interior.

Furthermore, it is conceivable that, due to a targeted movement or a targeted change in movement of the movement device, the pressure in the interior is varied in such a manner that the elastic element is at least locally deformed, in particular compressed, and subsequently relaxed. Depending on the pressure developing in the vessel interior, the inlet valve and/or the outlet valve are opened and closed so that suitable cultivation of the cells located on or in the elastic element can take place. Of course, it is also conceivable to at least intermittently supply culture medium to the vessel interior or discharge it therefrom via the valve openings in the inlet and/or outlet, if required. Both the quantity and the composition of the culture medium present in the vessel interior can be adjusted in this manner as a function of the physiological parameters required for cultivation of the respective cells arranged in the vessel interior.

By providing an inlet and/or outlet, it is thus possible, at least intermittently, to establish a flow channel for a flow of air, gas and/or liquid between the vessel interior and a fluid supply arranged outside the vessel interior or the environment.

In a further special embodiment, a bioreactor according to the invention has at least one closable access via which a connection to the vessel interior can be established at least intermittently. In this context, it is conceivable that a flow channel penetrating the vessel wall is at least intermittently opened via such an access, via which channel at least one medium comprising at least one nutrient, bacteria and/or a fluid is introduced into the vessel interior or discharged therefrom.

According to a particular refinement of the invention, a specially designed access is a sampling access through which at least part of the cells and/or culture medium located in the vessel interior can be removed. In this context, it is conceivable that at least intermittently, preferably automatically, a sample of the culture medium and/or the cells arranged in the vessel interior is taken and examined. Depending on the results of the examination, at least one parameter which has an influence on the cultivation of the cells is preferably varied as required. In this context, it is conceivable that, depending on an examination result, either the amount or composition of the culture medium located in the vessel interior is changed or the movement process of the movement device and thus of the moved elastic element is changed in a specific manner.

Moreover, alternatively or additionally to the sampling access, at least one access can be provided, which is provided at least in certain regions for the arrangement of a sensor element, for example a probe for detecting a pH value or an $O_2$ concentration, in the region of the vessel interior.

In order to effect a suitable movement of the movement device and thus deformation of the elastic element, the movement device can be coupled to at least one suitable drive unit, which in turn is controlled by means of a central control unit. It is conceivable that the drive unit has at least one mechanically, pneumatically, hydraulically, electrically or electropneumatically driven drive element which acts on the movement device to generate a movement.

According to a particular embodiment of the invention, the movement device has at least one piston which is set in motion by means of an electric, pneumatic or electropneumatic drive unit as required for the temporary deformation of the elastic element. The piston is moved here in such a manner that the elastic element arranged in the vessel interior is alternately compressed and relaxed, so that the cells arranged on or in the elastic element are stimulated due to the movement and are stimulated to a special growth. This introduction of movement stimuli facilitates the cultivation of the cells, for example the generation of a cell group, in a comparatively simple and trouble-free manner.

According to a further special configuration of a bioreactor according to the invention, the movement device has at least one membrane which at least partially closes off the vessel interior from the environment and is at least intermittently deformed during operation by a piston element connected directly or indirectly to the drive unit Preferably, the drive unit has a pneumatic cylinder whose movably mounted piston rod is connected, for example screwed, to the piston element.

In general, it is conceivable that the membrane contacts the elastic element at least intermittently during operation. Advantageously, the membrane is deformed, for example at least intermittently curved, due to a movement of the piston element so that as a result, the elastic element is also deformed in a suitable manner, in particular compressed or clinched.

In a particular embodiment, the piston element is adapted to carry out a stroke of 90 to 110 mm, in particular of about 100 mm, during operation. In this context, it is again conceivable that the piston element at least intermittently performs a linear or circular movement during operation.

Furthermore, a bioreactor designed according to the invention preferably has at least one sensor element that detects at least one parameter, in particular a physiological parameter, in the interior of the vessel. This can be the concentration of the culture medium, a composition of the culture medium, a temperature, a pressure, a gas concentration and/or another physiological parameter that has an influence on the cultivation of the cells arranged in the vessel interior on or in the elastic element Depending on a detected measured value and a relevant setpoint value, it is conceivable that a central control unit generates a control signal which is used to control a drive unit for initiating the movement of the movement device, a fluid supply and discharge and/or a dosing unit. In this manner, it is possible to selectively change a quantity, a composition and/or a concentration of the culture medium located in the vessel interior, its components and/or another substance. Here, the control unit generates suitable control signals preferably depending on a comparison between the measured value detected by at least one sensor element and a setpoint value which, for example, is stored in a database.

According to a very special embodiment, it is provided that the drive unit has at least one cam, which in turn is in operative connection with the movement device during its movement and initiates a movement that leads to an alternating compression and relaxation of the elastic element. The at least one cam which, for example, can be part of a shaft, preferably performs a rotational movement and thus initiates a movement of the movement device, such as a piston, arranged at least partially in the vessel interior, in different directions. According to a particular refinement of the invention, it is conceivable in this respect that a plurality of bioreactors are arranged next to one another in a suitable manner and the movement devices of the individual bioreactors are driven by means of a camshaft which has a plurality of cams.

Advantageously, at least one sealing element is provided between a movement device which at least intermittently causes a deformation of the elastic element and an inner wall of the vessel, by means of which sealing element the vessel interior is sealed in a fluid-tight, thus liquid-tight and/or gas-tight manner with against the environment. Such a sealing element can be designed, for example, in the form of an annular seal which surrounds the movement device, for example a piston of the movement device. In general, it is conceivable that the at least one sealing element is moved together with the movement device or that there is a relative movement between the sealing element and the movement device. In the latter embodiment, the at least one sealing element is preferably fixed at least in certain sections to a region of the inner wall of the vessel by means of suitable fixing elements.

According to another particular embodiment of the invention, it is conceivable that the movement device itself has an inlet and/or an outlet forming at least part of a flow channel between the vessel interior and a fluid supply or the environment. In this case, the inlet and/or outlet are thus not located in a wall of the vessel in the interior of which cells are cultivated but are located within the movement device. For example, it is conceivable that a piston which is mounted to be movable relative to the vessel wall has at least one such inlet and/or outlet, in which in turn a valve is arranged in an advantageous manner for selectively opening and closing the inlet and/or outlet.

A further special refinement of the invention provides that at least one fixing means is provided, which at least in certain regions fixes the elastic element within the vessel. Such a fixing means can comprise, for example, at least one hook element engaging in the elastic element in such a manner that a movement of the elastic element relative to the interior and/or the movement device is limited or even prevented at least in one direction. Generally, it is conceivable that the at least one fixing means is arranged on an inner wall of the vessel and/or on the movement device on a side facing the vessel interior. By means of such a fixing means or a plurality of fixing means, for example in the form of hooks, spikes or stops, it can be ensured that due to a movement of the movement device, the elastic element is moved specifically in at least one particular direction and/or that movements in at least one selected direction are prevented. Suitable selection and arrangement of corresponding fixing means ensure that specific movements of an elastic element, which is moved by means of a movement device, are generated inside the vessel and that the cells to be cultivated are stimulated in a suitable manner, in particular to provide improved growth conditions.

DETAILED DESCRIPTION

In the following, the invention will be explained in more detail by means of exemplary embodiments with reference to the figures without limiting the general idea of the invention.

Figure 1:
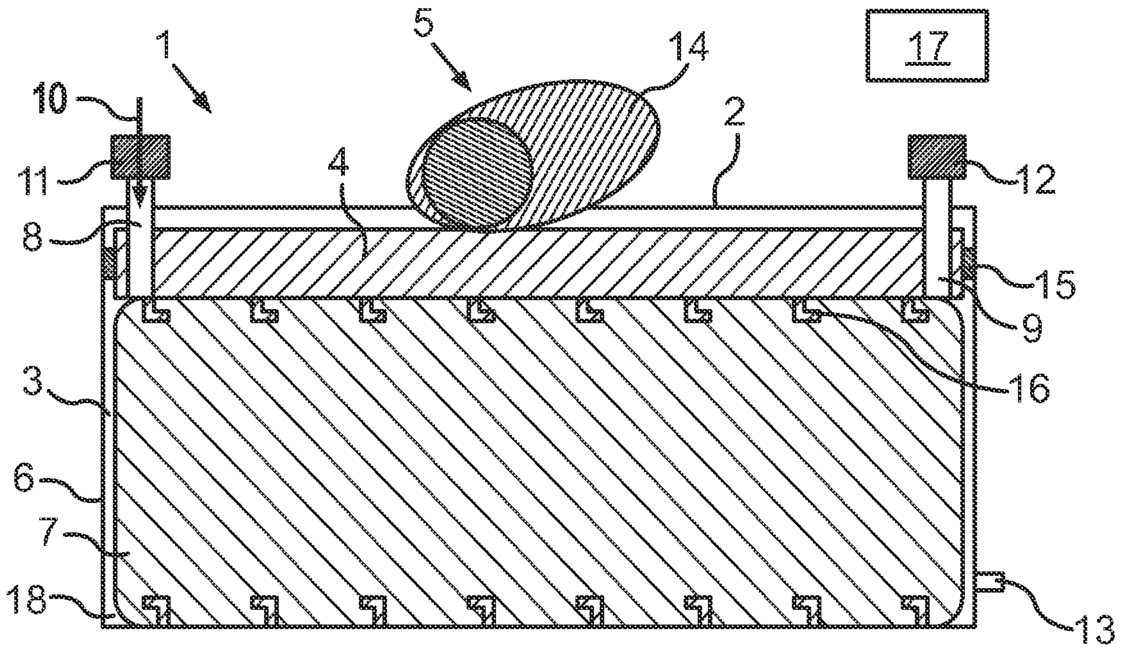
FIG. 1 shows a bioreactor according to the invention in an operating situation with relaxed elastic element.

FIG. 1 shows a bioreactor 1 designed according to the invention with a sterilizable vessel 2, in the vessel interior 3 of which an elastic element 7 in the form of a sponge and a movement device 4 mounted to be movable relative to the vessel wall 6 are arranged. The elastic element 7 is fixed in the vessel interior by means of hooks which serve as fixing elements 16. On the surface and in the pores of the elastic element 7, cells are arranged which are cultivated in a suitable manner so that large-area or even three-dimensional cell structures, for example muscle fibers or artificial meat, can be produced.

Essential for the bioreactor 1 shown in FIG. 1 is that the movement device 4, which according to the explained exemplary embodiment, has a piston which can be moved along an inner side of the vessel wall 6 and during an operation intermittently deforms the elastic element 7 in the vessel interior 3 with the cells adhering thereto, wherein the elastic element is alternately compressed and relaxed, resulting in a corresponding change in volume. For this purpose, the piston of the movement device 4 moves alternately in opposite directions, either into the vessel 2 or out of the vessel, so that suitably an alternate compression and relaxation of the elastic element 7 and thus a stimulation of the cells adhering to the elastic element takes place, whereby improved cell growth can be implemented. A further advantage is that the elastic element 7 which, in this case, comprises sponge-like material, alternately absorbs and releases culture medium 18, so that the cells are evenly supplied with the nutrients contained in the culture medium 18 and still come into sufficient contact with the gaseous atmosphere contained in the vessel interior, in particular with the oxygen and or $CO_2$ contained therein.

Between the piston of the movement device 4 and an inner side of the lateral vessel walls 6, a further sealing element 15 is provided, which ensures a reliable sealing of the vessel interior 3 against the environment According to the exemplary embodiment shown here, the sealing element 15 is designed in the form of a sealing ring and is attached to the piston of the movement device 4 so that it is moved together with the latter.

Figure 2:
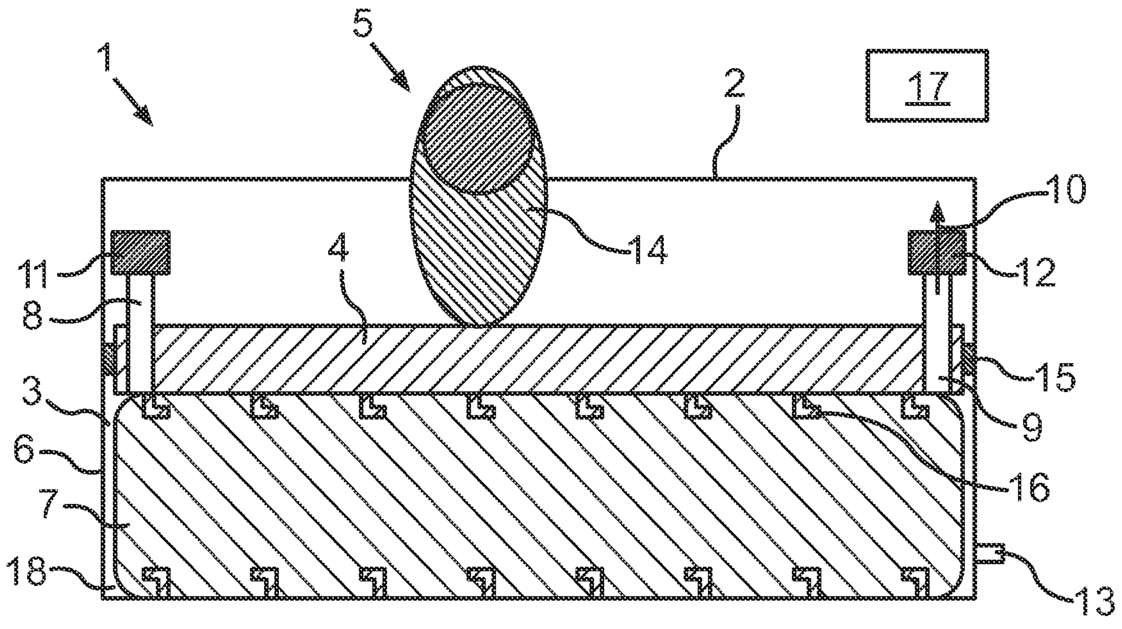
FIG. 2 shows a bioreactor according to the invention in an operating situation with compressed elastic element.

On a side opposite to the vessel interior 3, the movement device 4 is in operative connection with a drive unit 5 which as drive element 14 has a cam that is rotatably mounted and driven by an electric motor. A rotation of the cam causes the piston of the movement device 4 to move alternately either in the direction of the vessel interior or in the direction of the cam, wherein during the movement in the direction of the vessel interior 3, the elastic element 7 with the cells adhering thereto is compressed. This operating condition in which the elastic member 7 is compressed is shown in FIG. 2.

Hooks used as fixing elements 16 are arranged not only on the vessel wall 6 forming the bottom of the vessel 2, but also on that side of the piston of the movement device 4 that faces the vessel interior 3 and thus the elastic element 7. With these hook-shaped fixing elements 16, the elastic element is fixed in its position in the vessel interior 3 and, for example, an unintentional slipping is reliably prevented.

Furthermore, an inlet 8 with an inlet valve 11 and an outlet 9 with an outlet valve 12 are provided in the region of the piston of the movement device 4. Via the inlet, gas and/or culture medium 18 can be introduced into the vessel interior 3 from a corresponding fluid supply 10 and discharged accordingly via the outlet 9. Opening and closing the valves 11, 12 arranged in the inlet 8 and in the outlet 9 takes place here in dependence on the pressure prevailing in the vessel interior 3. Such a control of the valves 11, 12 has the great advantage that opening and closing the valves 11, 12 can be implemented in a comparatively simple and safe manner. Alternatively or additionally, it is conceivable to provide a central control unit 17 which generates suitable control signals for implementing an effective cultivation process and exchanges signals uni- or bidirectionally with the inlet and outlet valves 11, 12, but also with a drive unit 5, at least one sensor element, a fluid supply 10 and/or a device for specific temperature control of the vessel interior 3. A corresponding signal and/or data transmission can take place in a wired or wireless manner.

FIG. 1 shows a bioreactor 1 designed according to the invention in an operating state in which the piston of the movement device 4 is in a state moved out of the vessel interior 3, so that the elastic element 7 is relaxed and can at least partially receive culture medium 18.

In contrast, FIG. 2 shows a bioreactor 1 designed according to the invention in an operating state in which the piston of the movement device 4 is in a state maximally retracted into the vessel interior 3, so that the elastic element 7 is compressed to a minimum volume. In this case, the cam used as the drive element 14 of the drive unit 5 is rotated counterclockwise by about 260° to the left compared to the operating state shown in FIG. 1, as a result of which a corresponding movement of the piston has been initiated.

By selectively varying the shape of a cam and/or changing the rotational speed, both the degree of deformation and the speed at which the elastic element 7 arranged in the vessel interior 3 is deformed can be changed. Both the speed of a change in shape and the degree of a change in shape of the elastic element 7 take place in this case as a function of the parameters required for optimum cultivation of the cells arranged in the vessel interior 3 and in or on the elastic element 7.

By means of the bioreactor 1 shown in FIGS. 1 and 2, it is possible in a comparatively simple manner to set physiological growth parameters adapted to the respective cell type when cultivating cells of prokaryotic or eukaryotic origin. In particular, the type and magnitude of the stimuli which are to stimulate the cells to grow can be varied. A bioreactor 1 designed according to the invention enables the cultivation of special cell groups due to the application of external stimuli on a larger scale. Furthermore, even three-dimensional tissue structures for medicine or muscle fibers as starting material for cultivated meat can be produced. In this regard, a bioreactor designed according to the invention has the three main components shown in FIGS. 1 and 2, namely a sterilizable vessel 2, a movement device 4 with a piston, an alternately compressed and relaxed elastic element 7, and a fluid supply with an inlet 8 and an outlet 9 for the required gas exchange.

Furthermore, an access 13 is provided, which according to the illustrated exemplary embodiment is provided for taking samples of the culture medium 18 and/or the cells arranged in the vessel interior 3 as needed.

According to the special embodiment of the invention described here, the elastic element 7 is formed as a sponge made of glucomannan. However, depending on the cells to be cultivated in each case, the elastic element can also comprise other materials which are suitable for serving as a carrier for the cells to be cultivated and which can at least partially receive culture medium 18. By means of at least one suitable fixing element, the elastic element 7 can be fixed in the vessel interior 3 in an advantageous manner. For this purpose, the configurations shown in FIGS. 1 and 2 provide that hooks for anchoring are arranged on the bottom of the bioreactor 1 and on the underside of the piston of the movement device 4. The elastic element 7 serves in each case as a structural matrix for the attachment of the cells to be cultivated.

Figure 3:
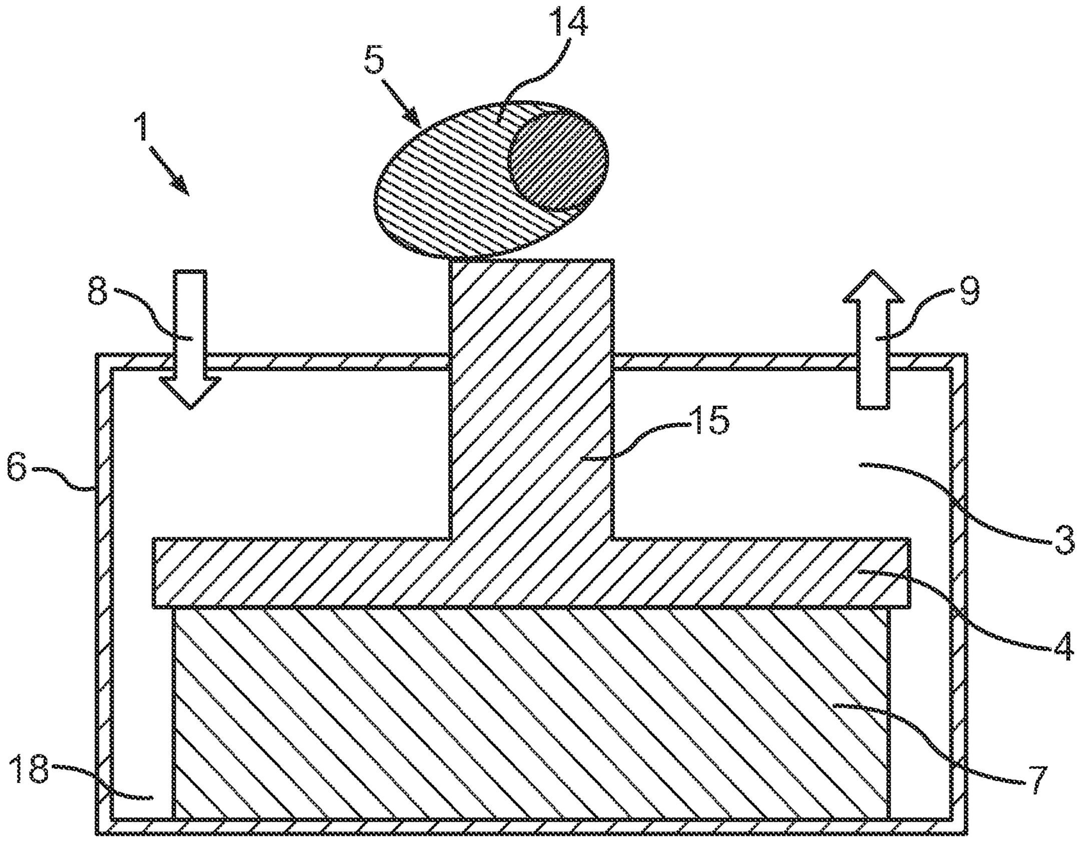
FIG. 3 shows a schematic illustration of a bioreactor according to the invention, the movement device of which has a piston and a piston rod.

FIG. 3 additionally shows a schematic illustration of a bioreactor 1 designed according to the invention, the movement device 1 and fluid supply of which, however, are designed differently from the bioreactor 1 shown in FIGS. 1 and 2. The functional principle essential to the invention, namely the compression of an elastic element 7 arranged in the vessel interior 3 together with the cells to be cultivated adhering thereto, which compression is effected by a movement device 4, is also implemented with the device shown in FIG. 3. The essential difference to the bioreactor 1 shown in FIGS. 1 and 2 is that the movement device 4 comprises a piston and a piston rod which establishes the connection between the piston acting on the elastic element 7 in the vessel interior 3 and a drive unit 5 arranged outside the vessel 2. According to this embodiment, the piston rod protrudes through the vessel wall 6 such that a comparatively small sealing element 15 is arranged between the sealing surfaces of the vessel wall 15 and the piston rod. In this case, the supply and discharge of at least one fluid into and/or out of the vessel interior 3 is takes place via an inlet 8 and an outlet 9 which are arranged within the vessel wall 6 and thus establish a connection between the vessel interior 3 or a fluid supply system (not shown in this view). The remaining components, such as different accesses or a control unit, as shown in FIGS. 1 and 2, cannot be seen in the schematic illustration according to FIG. 3, but can also be used in this special embodiment without limiting the general idea of the invention.

The movement of the movement device 4 and thus of the elastic element 7 in the vessel interior 3 is generated by means of a suitable drive unit 5. For this purpose, the drive unit 5 in the figures has a cam as a drive element 14 which can be part of a camshaft and, due to its movement, initiates an up and down movement of the piston. Of course, it is also conceivable to implement the invention by means of other drive units, drive elements and/or movement devices than those shown in the figures. It is always essential to the invention that an elastic element with cells adhering thereto is arranged inside the vessel of the bioreactor, which elastic element is alternately deformed, in particular compressed and relaxed, by means of a movement device. Advantageously, a sponge-like material which can be of synthetic or natural origin is used for such an elastic element. Here, the physically induced stimulation of the cells to be cultivated is achieved by the mechanical compression and relaxation of the elastic element forming the cell-containing matrix. In this manner, not only the required gas supply, in particular the air exchange via the valves arranged in the inlet and outlet is implemented, but at the same time also a constant, homogeneous supply of nutrients by the culture medium which is alternately absorbed and released by the elastic element.

Thus, a bioreactor designed according to the invention represents a simple and efficient technical solution for stimulating cells and biofilms for the desired phenotypic transformation, for example, differentiation of myoblasts into microtubules. Furthermore, such a bioreactor is easily scalable, has components that are comparatively wear-resistant and enables particularly gentle cell cultivation.

Figure 4:
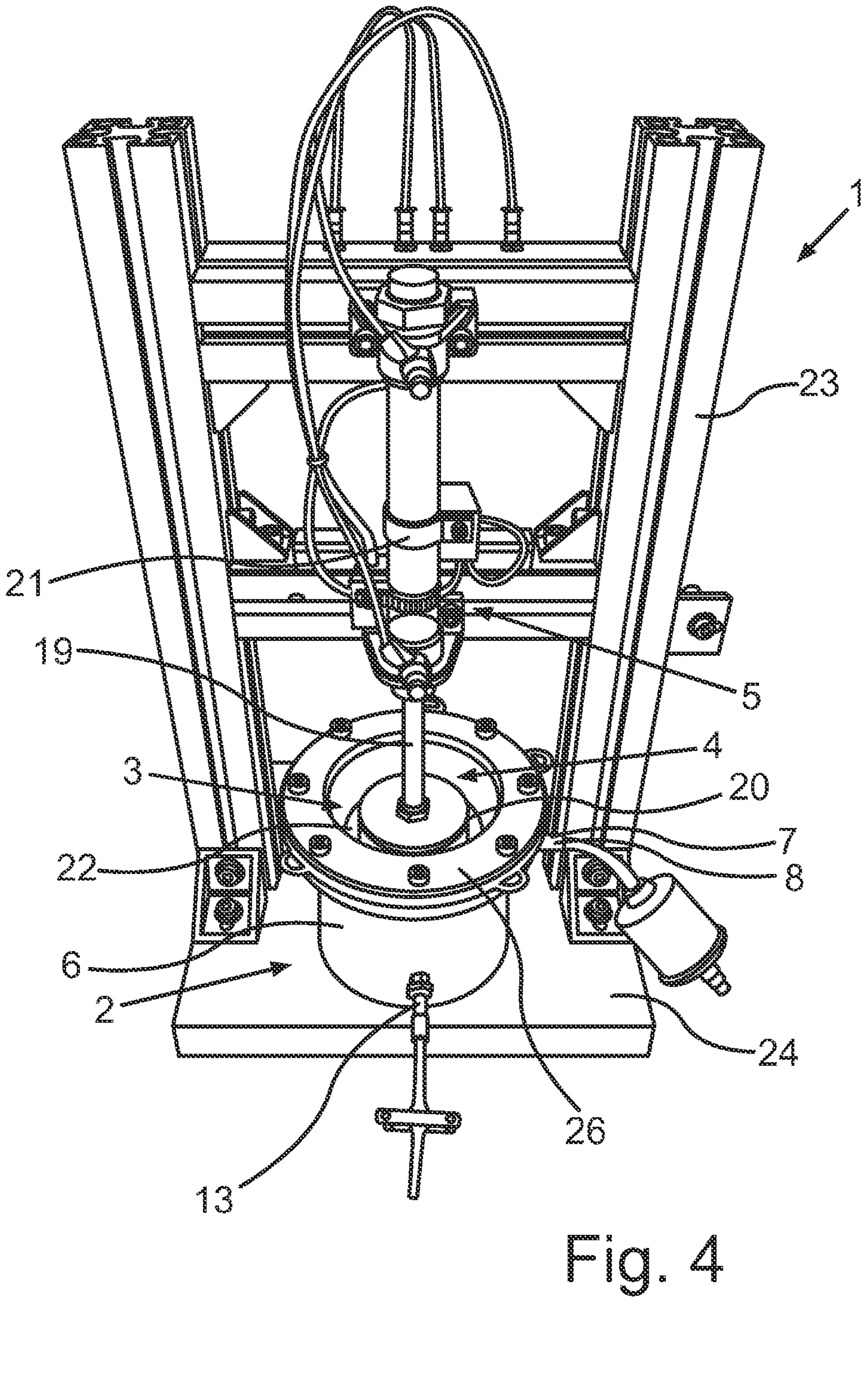
FIG. 4 shows a picture of a special embodiment of a bioreactor designed according to the invention.

Furthermore, FIG. 4 shows a special embodiment of a bioreactor 1 designed according to the invention. By means of a prototype, the general functionality of such a bioreactor 1 has already been demonstrated using an elastic element, in or on which no cells were provided, and water as culture medium 18.

The bioreactor 1 shown in FIG. 4 has a drive unit 5 with a pneumatic cylinder 21 pressurized with compressed air in which a piston rod 19 is guided, the end of which facing the vessel 2 is connected to a piston element 20 of the movement device 4. The tests were carried out with a double-acting pneumatic cylinder 21 ZDM 25/100 according to ISO 6432, the piston rod 19 of which has an outer diameter of 25 mm and which carries out a maximum stroke of 100 mm. The pneumatic cylinder 21 is mounted on a frame 23 which is made of stainless steel and has a base plate 24 as its base. The movement device 4 also has a membrane 22, in this case a silicone membrane, which closes off the vessel interior 3 of the vessel 2 at the top from the environment and which, in operation, is deformed by the piston element 20 during a movement of the piston rod 19 and as a result is moved at least intermittently downwards in the direction of the elastic element 7 which is arranged in the vessel interior 3 and is compressed as a result.

Furthermore, the bioreactor 1 shown in FIG. 4 has a vessel 2 with a lower connection with a spout as access 13 for sampling and a connection with a spout combining an inlet 8 and an outlet 9 for gas exchange. A silicone hose with a hose clamp for shut-off is fixed to the lower spout while a silicone hose with a hydrophobic PTFE air filter (PTFE=polytetrafluoroethylene) is connected at the top. On the flat vessel bottom, a round and internally hollow elevation made of stainless steel and provided with holes is arranged to accommodate an elastic element 7.

For a special test run, the movement of the piston element was set to 4-5 cycles per minute, with one cycle corresponding to an upward and downward movement. A commercially available Konjac sponge made of glucomannan from BlueFox was used as the elastic element 7, which forms a three-dimensional structure during operation, for example, for the production of artificial meat or for bacterial biofilm formation. Before the use in the bioreactor 1, this sponge forming the elastic element 7 was autoclaved in 100 ml of phosphate-buffered saline (PBS) with a composition of 8.0 g sodium chloride (NaCl), 0.2 g potassium chloride (KCl), 1.42 g disodium hydrogen phosphate ($Na_2HPO_4$), 1.78 g disodium hydrogen phosphate dihydrate ($Na_2HPO_4 \cdot 2H_2O$), and 0.27 g potassium dihydrogen phosphate ($KH_2PO_4$), pH 7.4, and placed in 100 ml of fresh phosphate buffered saline (PBS) overnight at room temperature.

To perform the test, the elastic element 7, here the Konjac sponge, was placed on the elevation and about 350 ml of liquid was filled into the vessel interior 3 so that the sponge was well saturated and half of it was in the liquid.

The vessel interior 3 is separated from the environment by a membrane 22, in this case a commercially available round silicone lid with a diameter of at least 15 cm, wherein the membrane 22 forms part of the movement device 4 for specific deformation of the elastic element 7. The membrane 22 is fixed by a metal ring 26 on the upper side of the vessel wall 6 by means of screws.

During operation, the pneumatic cylinder of the drive unit 5 was pressurized with compressed air at a pressure of 4-5 bar (0.4-0.5 MPa) and the piston rod 19 was moved in the desired pumping cycle of 4-5 cycles per minute. The piston rod 19 and the piston element 20 attached thereto are arranged centrally directly above the membrane 22 in such a manner that, in operation, the piston element 20 presses the membrane 22 downward during a downward movement and the membrane surface, at least in a central region, bulges downward at least 5 cm, thereby deforming the elastic element 7 in the form of the Konjac sponge, forcing culture medium 18 out of the elastic element 7 and displacing air from the vessel interior 3. During an upward movement of the piston element 20, in turn, air flows into the vessel interior 3 and the elastic element 7 sucks in culture medium 18. A commercial incubator was used as the vessel 2 for the test run, and the test was conducted at an ambient temperature of 27° C. for at least 24 hours. It was found that the prototype was fully functional and exhibited stable operating behavior over a long period of time.

Figure 5:
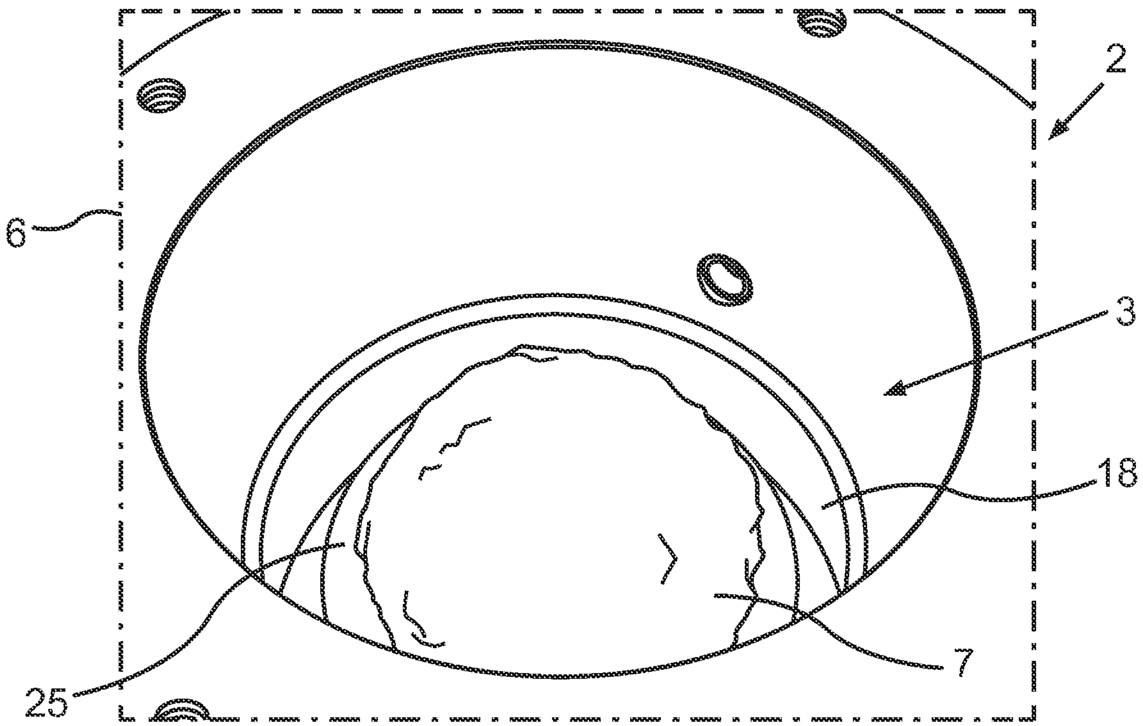
FIG. 5 shows a picture of an embodiment of the opened vessel of a bioreactor designed according to the invention with the elastic element which is arranged in the vessel interior and lies on an elevation of the vessel bottom.

In addition, FIG. 5 shows the opened vessel 2 with the elastic element 7 which is arranged in the vessel interior 3 and lies on an elevation 25 of the vessel bottom. The elastic element 7 shown here, which forms a three-dimensional structure during operation, for example for the production of artificial meat or for bacterial biofilm formation, is a commercially available Konjac sponge made of glucomannan from the company BlueFox. Before being placed in the vessel interior 3 of the bioreactor 1, this sponge forming the elastic element 7 was autoclaved in 100 ml of phosphate-buffered saline (PBS) with a composition of 8.0 g sodium chloride (NaCl), 0.2 g potassium chloride (KCl), 1.42 g disodium hydrogen phosphate ($Na_2HPO_4$), 1.78 g disodium hydrogen phosphate dihydrate ($Na_2HPO_4.2H_2O$), and 0.27 g potassium dihydrogen phosphate ($KH_2PO_4$), pH 7.4 and placed in 100 ml of fresh phosphate-buffered saline (PBS) overnight at room temperature.

In the following, the cultivation of the bacterial strain Streptomyces spec. using a bioreactor 1 designed according to the invention is described as an example, wherein Streptomyces sp. DSM No.: 40434 (DSMZ, Germany) was used for the initial growth test in the new bioreactor 1. The Streptomyces strain was grown in 50 ml of complete medium 2YTPG (16 g/L tryptones, 10 g/L yeast extract, 5 g/L sodium chloride (NaCl), 5 g/L glucose, 3 g/L potassium dihydrogen phosphate (KH2PO4), 9 g/L dipotassium hydrogen phosphate ($K_2HPO_4$-$3H_2O$) in a 250 ml baffled Erlenmeyer flask and incubated at 180 rpm and 28° C. for 24 hours. Cells were then pelletized in a 50 ml reaction vessel at 4700 rpm for 10 min and then resuspended in 25 ml minimal medium R2 (Hopwood D. A., Bibb M. J., Chater K. F., Kieder T., Bruton C. J., Kieser H. M., Lydiate D. J., Smith C. P., Ward J. M., Schrempf H. 1985. Genetic manipulation of Streptomycetes—a laboratory manual. The John Innes Foundation, Norwich) for pigment formation. The cells were added to 325 ml of minimal medium in a bioreactor 1 designed as shown in FIG. 4 and incubated at 28° C. for >72 hours. Instead of an elastic element 7 made of glucomannan, a commercial polyurethane sponge was used as the elastic element. For this test run, the flask movement was set to 4-5 cycles per minute. Cells could be detached from elastic element 7 after completion of the test run for fermentation, visible by turbidity of the medium. Under a microscope (Olympus BX41), hyphae structures typical of streptomyces were clearly visible. The antibiotic and pigment actinorhodin produced by the bacteria could be extracted with methanol and caused the specific red coloration of the solution. The pigment formation showed that a bioreactor 1 formed according to the invention can be used for the production of industrially relevant substances, such as antibiotics.

In a further test, red fluorescent protein tdTomato was produced in *E. coli* using a bioreactor 1 designed according to the invention, which in turn was designed according to the special configuration shown in FIG. 4. Here, the production of a recombinant protein was investigated as a further test object for the bioreactor 1.

The aim was to produce red fluorescent protein tdTomato, which is already optically visible in daylight and acts as a pigment. Plasmid pUC57_T7_td-tomato was transformed into chemically competent BL21-AI One Shot *E. coli* cells according to the manufacturer's instructions (Thermo Fisher Scientific) and plated on LB agar plates, consisting of yeast extract (5 g/L), tryptone (10 g/L), sodium chloride (0.5-10 g/L), and agar (15 g/L) (pH adjusted to 7 with NaOH), with 100 μg/ml ampicillin and incubated at 37° C. overnight. One colony was used to inoculate a test tube with 5 ml of fresh LB medium the next day and incubated overnight at 37° C. and 160 rpm. A glycerol stock containing 25% (w/v) sterile glycerol was made from this culture the next day and used as a starting point for all further tests. In a 250 mL baffled Erlenmeyer flask, the strain was grown as a preculture in 50 mL of medium without induction and allowed to grow overnight at 37° C. and 200 rpm. Then, a bioreactor 1 designed according to the embodiment shown in FIG. 4 was prepared and filled with 300 mL of medium. Thereafter, the cells were pelleted from 50 ml of the preculture in a 50 ml reaction vessel and resuspended in 50 ml of fresh medium. Subsequently, the solubilized cells were added to the medium in the bioreactor 1, the bioreactor 1 was sealed, and were incubated overnight at 37° C. at 2-3 pump cycles per minute. For the bioreactor run, the piston movement was set to 4-5 cycles per minute. The next day, cells, clearly producing the red pigment and thus the recombinant protein tdTomato, could be extracted from the sponge material of the elastic element 7. This illustrated that a bioreactor 1 designed according to the invention can be used for the production of recombinant proteins.

In a further special test, the functionality of a bioreactor 1 designed according to the invention for the cultivation of mammalian cells was to be demonstrated. Here, the mammalian cell line C2C12 was to be cultivated, which is an immortalized myoblast cell line from *Mus musculus* (see Yaffe, D., Saxel, O. Serial passaging and differentiation of myogenic cells isolated from dystrophic mouse muscle. Nature 270, 725-727 (1977)) and is suitable for demonstrating growth of muscle cells and their precursors because of its stable growth. The C2C12 cell line shows rapid differentiation and forms contractile myotubes and produces characteristic muscle proteins. Before the start of the test, a bioreactor 1 designed as shown in FIG. 4 was disassembled into its individual parts which were wrapped in aluminum foil, sterilized by autoclaving, and assembled under a sterile bench. A Konjac sponge (Bluefox, white) was used as the elastic element 7, was placed in 100 ml of PBS (phosphate-buffered saline) and autoclaved after swelling. Then, the elastic element 7 was placed in sterile and fresh 100 ml PBS and incubated with 0.001% poly-L-lysine for coating for better adhesion. Thereafter, the elastic element 7 was washed three times with 100 ml of sterile PBS each time. As medium, 350 ml of Dulbecco's Modified Eagle's Medium with glucose but without pyruvate (DMEM) was used. For inoculation, $2*10^7$ cells were used and added to the medium alongside the elastic element 7 of glucomannan. The bioreactor 1 was sealed with a membrane 22 made of silicone and placed under the drive unit 5. This was followed by incubation for at least 72 hours at two to three piston movements per minute at an ambient temperature of 37° C. with 5% $CO_2$ in the incubator atmosphere. After at least 72 hours, the reactor was opened under a sterile bench, the elastic element 7 in the form of a glucomannan sponge was washed with PBS and then examined microscopically. The microscopic inspection was performed using the Leica DM IL LED inverted laboratory microscope. Contamination with bacteria was not detectable. After trypsinization of the glucomannan material, SYTO9 fluorescent dye (Thermo Fisher Scientific) with the excitation wavelength of 485 nm and emission wavelength of 498 nm was used to stain the detached cells and detect live cells. By means of microscopic analysis, significant fluorescence of C2C12 cells from the glucomannan fraction was detected. Thus, cell growth was detected on the material from glucomannan in the bioreactor 1 designed according to the invention and the bioreactor's suitability for growing animal cells was demonstrated.

REFERENCE LIST

1 bioreactor
2 vessel
3 vessel interior
4 movement device
5 drive unit
6 vessel wall
7 elastic element
8 inlet
9 outlet
10 fluid supply
11 inlet valve
12 outlet valve
13 access
14 drive element
15 sealing element
16 fixing element
17 control unit
18 culture medium
19 piston rod
20 piston element
21 pneumatic cylinder
22 membrane
23 frame
24 base plate
25 elevation
26 metal ring

What is claimed is:

1. A bioreactor (1) for cultivation of cells, the bioreactor (1) comprising:

a vessel (2) having walls (6) around an interior (3), which is adapted to accommodate the cells to be cultivated and culture medium;

a movement device (4) comprising a membrane (22) which closes off the vessel interior (3) from an outer environment and is connected to a drive unit (5) having at least one mechanically, pneumatically, hydraulically, electrically or electropneumatically driven drive element (14) that drives a piston element (20) against the membrane (22);

an elastic element (7) within the vessel interior (3) that at least intermittently contacts the membrane (22) so that continuing to drive the piston element (20) against the membrane (22) deforms the membrane (22) and the elastic element (7) without deformation of the walls (6) and without the piston element (20) entering the vessel interior (3), the elastic element (7) configured to accommodate at least part of the culture medium and accommodate at least intermittent adherence of the cells to be cultivated so that the deformation of the elastic element (7) moves the cells or apply a force to the cells; and at least one closable inlet (8) and at least one closable outlet (9), through which a flow channel for an air and/or gas flow between the vessel interior (3) and a fluid supply (10) or the environment is established at least intermittently, wherein an inlet valve (11) is arranged in the at least one closable inlet (8) and an outlet valve (12) is arranged in the at least one closable outlet (9) and are designed in such a manner that opening and closing the inlet valve (11) and/or the outlet valve (12) is effected by a pressure change in the vessel interior (3).

2. The bioreactor according to claim 1, characterized in that the elastic element (7) comprises a sponge configured to at least intermittently adhere to the cells, absorb the culture medium, and deform by the movement device (4), which releases absorbed culture medium from the sponge.

3. The bioreactor according to claim 1, characterized in that the elastic element (7) comprises a foam configured to at least intermittently adhere to the cells, absorb the culture medium, and deform by the movement device (4), which releases absorbed culture medium from the foam.

4. The bioreactor according to claim 1, characterized in that the elastic element (7) comprises in vitro meat, bacteria, at least one polymer, a protein structure, glucomannan, zein, collagen, alginate, chitosan and/or cellulose.

5. The bioreactor according to claim 1, characterized in that the vessel (2) further comprises at least one closable access (13) via which a connection from outside the vessel (2) to the vessel interior (3) is established at least intermittently.

6. The bioreactor according to claim 1, characterized in that the elastic element (7) is configured to compress and relax over successive time intervals.

7. The bioreactor according to claim 1, characterized in that the at least one drive element (14) comprises a rotatably mounted cam which initiates movement of the piston element (20).

8. The bioreactor according to claim 1, characterized in that during operation, the membrane (22) contacts the elastic element (7) at least intermittently.

9. The bioreactor according to claim 1, characterized in that during operation, the piston element (20) is adapted to carry out a stroke of 90 to 110 mm.

10. The bioreactor according to claim 9, characterized in that during operation, the piston element (20) at least intermittently performs a linear or circular movement.

11. The bioreactor according to claim 1, further comprising a sealing element (15) arranged at least in regions between the movement device (4) and the vessel (2), wherein the sealing element (15) seals the vessel interior (3) in a liquid-tight and/or gas-tight manner against the environment.

12. The bioreactor according to claim 1, characterized in that the elastic element (7) is at least partially surface-treated.

13. The bioreactor according to claim 1, further comprising at least one fixing element (16) configured to fix the elastic element (7) to an inner side of at least one vessel wall (6) facing the vessel interior (3) and/or to the movement device (4).

14. A method of cultivating mammalian cells, comprising culturing mammalian cells in the bioreactor of claim 1.

* * * * *